United States Patent [19]

Haugk

[11] Patent Number: 5,334,387

[45] Date of Patent: Aug. 2, 1994

[54] TOPICAL COMPOSITION COMPRISING MONO AND DIALKYL PHOSPHATES WITH A COSURFACTANT

[75] Inventor: Peter D. Haugk, Lincoln Park, N.J.

[73] Assignee: Colgate-Palmolive Company, Piscataway, N.J.

[21] Appl. No.: 23,829

[22] Filed: Feb. 23, 1993

[51] Int. Cl.$^5$ .................................................. A61K 7/06
[52] U.S. Cl. ...................................... 424/401; 424/57; 424/70; 252/DIG. 5; 252/DIG. 13; 252/DIG. 14; 252/173; 252/174.16; 252/117; 252/132; 252/546
[58] Field of Search ............................ 424/57, 70, 401; 252/DIG. 5, DIG. 13, DIG. 14, 173, 174.16, 117, 132, 546

[56] References Cited

U.S. PATENT DOCUMENTS

| | | | |
|---|---|---|---|
| 4,139,485 | 2/1979 | Imokawa et al. | 252/135 |
| 4,511,513 | 4/1985 | Guth et al. | 260/404.5 |
| 4,554,097 | 11/1985 | Schebece et al. | 252/542 |
| 5,139,781 | 8/1992 | Birtwistle et al. | 424/401 |

Primary Examiner—C. Warren Ivy
Assistant Examiner—Zinna N. Davis
Attorney, Agent, or Firm—Martin B. Barancik; Robert C. Sullivan

[57] ABSTRACT

A composition suitable for topical application to the skin or hair comprising an admixture of a. phosphate surfactant mixture of structure (1) and (2) and b. a co-surfactant of formula (3).

16 Claims, No Drawings

TOPICAL COMPOSITION COMPRISING MONO AND DIALKYL PHOSPHATES WITH A COSURFACTANT

BACKGROUND OF THE INVENTION

Over the years there has been a constant evolution of cleansing compositions for the human skin. From the basic use of lye soap to the more advanced combars and synthetic detergents compositions in both liquid and solid form, there has been a constant quest for improved compositions having better cleansing activity but with increased mildness to the skin as well as inter alia, better sensory attributes.

Although sulfates and carboxylates are still commonly used as surfactants, in the last few years attention has been drawn to phosphates utilized for that function. U.S. Pat. No. 4,139,485 issued Feb. 13, 1979 to Kao Corporation is directed to a composition utilized for skin care employing a mixture of two different phosphates, a monoalkyl phosphate and dialkylphosphate, the proportion of the dialkyl phosphate, if present at all, to be no more than 20 weight percent of the total mono and dialkylphosphate. Above 20 weight percent, the composition is stated to have substantially inferior foaming properties, water solubility and is unsuitable for use in detergent compositions of that invention, see column 7, lines 46–55 of U.S. Pat. No. 4,139,485. Recently U.S. Pat. No. 5,139,781 issued Aug. 18, 1992 to Cheseborough Ponds disclosed that the special proportions of monoalkylphosphate to dialkylphosphate necessary for proper foaming, water solubility and mildness of the previously mentioned Kao U.S. Pat. No. 4,139,485 were not necessary as long as there was at least one of a very limited family of co-surfactants also present in the composition. These cosurfactants were limited to either an alkylamidopropyl betaine or an alkylamphoglycinate. A host of additional supplementary surfactants could also be present but the two previously mentioned betaines or glycinates were critical to improving the foaming of the compositions as measured by foam height, perceived volume and creaminess. The additional supplementary surfactants were exhaustively described at column 5, line 25 through column 9, line 52 of the 781 patent.

It has now been discovered that a new cosurfactant group can be combined with mono and dialkylphosphate, ethoxylated or not, with levels of dialkylphosphate significantly above 20 wt %, as measured by total wt % mono and dialkyl phosphate and obtain a detergent composition which is mild, water soluble and produces a foam which enhances cleaning, and has specific advantages in flash foaming and total foam height.

SUMMARY OF THE INVENTION

In accordance with the invention, there is a composition suitable for topical application to the skin or hair comprising an admixture of:

a phosphate surfactant mixture of the structure

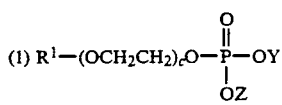

and

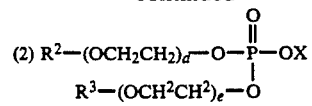

wherein $R^1$ is normal alkyl having an average of from about 10 to 18 carbon atoms, preferably 12 to 18;

$R^2$ and $R^3$ are the same or different and are normal alkyl having an average of about 10 to 18 carbon atoms, preferably 12 to 18;

X, Y and Z are the same or different and are selected from hydrogen, alkali metal, ammonium and substituted ammonium cations;

d and e are the same or different and are selected from 0 or an integer from 1 to 10; and c is 0 or an integer from 1 to 4; wherein with respect to a (1) and a (2) taken together the wt % of a (1) is from about 55 to 75 wt % and a (2) is from about 25 to 45 wt %, and b. a cosurfactant of the formula

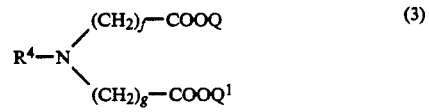

wherein $R^4$ is normal alkyl having an average of from about 10 to 18 carbon atoms;

f and g are the same or different and are 1 or 2;

Q and $Q^1$ are the same or different and are selected from hydrogen, alkali metal, ammonium, and substituted ammonium cation with the proviso that Q and $Q^1$ are not hydrogen at the same time; wherein with respect to a and b taken together, a is from about 33 to 95 wt % and b is from about 5 to 67 wt %.

A further aspect of the invention is the composition identified above consisting essentially of a and b.

A still further aspect of the invention is the identified compositions wherein less than 1 wt % of the composition is the co-surfactant utilized in U.S. Pat. No. 5,139,781, an alkylamidopropyl betaine and/or an alkylamphoglycinate, as defined in U.S. Pat. No. 5,139,78at column 2, line 50 to column 3, line 4, incorporated herein by reference. It is preferred to have the aforementioned glycinate and/or betaine essentially absent, for example less than 0.2 wt % or, even more preferably, absent from the claimed composition of this case.

Additionally, further phosphate salts wherein the long chain group, i.e. "R" has a carboamide group therein are preferably also limited to less than 1 wt % of the composition, are essentially absent (or less than 0.2 wt % of the composition) or are absent from the composition.

DETAILED DESCRIPTION OF THE INVENTION

The composition according to the invention is intended as a personal washing product for cleansing the face and other sensitive parts of the body surface, including the mucosas. It can also be used for washing the hair as well as the skin. Other uses for the composition such as sharing foam and the like involving multiple phase or solid compositions are also covered by the invention.

With respect to the phosphate surfactant and cosurfactant, illustrative examples of the R group include decyl, undecyl, dodecyl, myristyl, palmityl and stearyl. R groups of 12–14 carbon atoms are preferred.

The values for c, d and e are preferably 1 to 4, most preferably 3.

Typical of the alkali metals for X, Y and Z are sodium and potassium. Exemplification of substituted ammonium salts include those cations produced from amines used for neutralization of the corresponding phosphoric acids by quaternization after the neutralization step in the process for preparing monoalkyl phosphate salts of formula (1). The corresponding amines are primary, secondary and tertiary amines having alkyl groups of 1 to 3 carbon atoms which may be further substituted, particularly by hydroxyl groups. As the amines, there may be mentioned, for example, dimethylol monoethanolamine, methyldiethanolamine, trimethylamine, triethylamine, dibutylamine, butyldimethylamine, monoethanolamine, diethanolamine, triethanolamine, isopropyldimethylamine and isopropylethanolamine as well as tris (hydoxymethyl) amino methane. Preferred amines are monoethanolamine, diethanolamine and triethanolamine. A particularly preferred amine is triethanolamine.

The values for f and g are preferably the same and are 2.

With respect to the ratio of a (1) and a (2) there is preferably 60 to 70 wt % a (1) and 30 to 40 wt % a (2). Preferably the wts. of a in a and b together is about 50 to 90 wt % a and 10–50 wt % b, more preferably about 70 to 85 wt % a and 15 to 30 wt % b.

The composition according to the invention also comprises an amount of water to act as a vehicle for a liquid composition for the phosphate and cosurfactant. It enables them to be provided at a concentration suitable for convenient topical application to human skin.

The composition according to the invention can also have optionally any one or more known agents satisfying various functions known to be useful in topical skin care, particularly for facial cleansers. Examples of these functions are additional surfactants such as anionic surfactants other than the a and b salts defined herein as well as nonionic, amphoteric and zwitterionic surfactants. Additional functions include agents operating as thickening agents, preservatives, emollients, solvents, humectants, thickeners, and powders. Example of these further agents appear at the aforementioned U.S. Pat. No. 5,139,781 column 5, line 35 to column 11, line 33 all of which is herein incorporated by reference into this present specification. Certain of these additional surfactants and additives bring about preferred compositions because of their contributions to foaming, clarity, freeze thaw stability, viscosity stabilization and the like of the compositions.

The composition according to the invention can take the form of a liquid or gel, intended to be dispensed from a capped container such as a bottle, roll-on applicator or tube or a pump-operated or propellant driven aerosol dispenser, as a skin cleanser, shower product, bath additive or shampoo. The composition can also take form of a powder or a solid such as a stick, preferably housed in a suitable capped holder with a wind-up or push-up action similar to a lip stick, or a bar or tablet intended to be used for washing instead of a conventional soap bar.

The invention further provides a closed container containing a detergent composition as herein defined.

The invention further provides a process for preparing the composition of the type defined herein, which process comprises the steps of:

(i) preparing a mixture comprising one or more dialkyl phosphate surfactants, as defined herein, and one or more monoalkyl phosphate surfactants, as defined herein in a, and one or more co-surfactants, as defined herein in b; and (ii) subsequently packaging the mixture into containers.

As stated previously, the preferred compositions are the liquid cleansers utilized on the skin, for example the hand and face. The addition of the component b to the mono and di alkyl phosphates a(1) and a(2) maintained the clarity of the phosphate based solution or improved it while bringing about increased foam potential. As shown, by the data below, the use of component b was highly selective since numerous other surfactants failed to provide the desired clarity for the liquid hand and facial (body) cleanser composition in combination with the overall mildness and foaming characteristics.

Cosurfactants were added to enhance the performance of the primary surfactant system in the cleansing system. Cosurfactants designed to enhance the performance of the phosphate blend were chosen for testing based on their expected superior mildness and good foaming properties. The formulations were prepared having the following composition.

EXAMPLE 1

| Ingredient | | % w/w |
| --- | --- | --- |
| Part 1 | | |
| Monolaureth-3 Phosphate | | 13.80 |
| Dilaureth-3 Phosphate | | 6.20 |
| PEG-40 Stearate | | 3.00 |
| Polysorbate 60 | | 2.50 |
| PEG-25 Hydrogenated Castor Oil | | 2.00 |
| Pareth 25-7 Carboxylic Acid | | 1.00 |
| PEG-150 Distearate | | 3.00 |
| Part 2 | | |
| Deionized Water | q.s. to | 100.00 |
| NaOH (50% aq.) | | 4.85 |
| Cosurfactant | | See Table 1 |
| Part 3 | | |
| Deionized Water | | 4.00 |
| FD&C Blue #1 (0.01% aq.) | | 1.20 |
| Part 4 | | |
| DMDM Hydantoin | | 0.30 |
| Fragrance | | 0.30 |
| | | 100.00 |

Batches were prepared as follows. Ingredients of Part 1 were weighed together and heated to 60°–65° C. with slow mixing. Part 2 ingredients were then added one by one to Part 1 and agitation increased to moderate speed while avoiding aeration. The temperature of the batch was then increased to 80°–82° C. and maintained at this temperature for 30 minutes. After 30 minutes, the batch was then cooled to 55° C. with slow stirring and each ingredient of Part 3 added in order. The batch was then cooled to 40° C. and the ingredients of Part 4 were added while continuing to mix at low speed. The batch was then cooled to 25° C. and evaluated for pH and clarity immediately after preparation. pH values generally fell within the range of 7.4–7.7.

As is observed from the component list, additives such a preservative (dimethyl dimethylol hydantoin, (DMDM hydantoin), a thickener (PEG 150 distearate), polysorbate 60 and the like are also present in the formulation.

The results of cosurfactant testing are provided in Table 1.

TABLE 1

| Cosurfactant | % by wgt. | Clarity |
|---|---|---|
| 10% water (no cosurfactant) | 0 | Clear |
| Mixture of special fatty alcohol ether sulfates [Texapon ASV (26%)] | 10 | Opaque |
| Cocamidopropyl Betaine (35%) | 10 | Translucent |
| Sodium Lauroyl Sarcosinate (30%) | 10 | Translucent, fades blue color |
| Disodium Laureth Sulfosuccinate (and) Sodium Lauryl Sulfoacetate (25%) | 10 | Opaque |
| Sodium Methyl Cocoyl Taurate (24%) | 10 | Opaque |
| Disodium Laureth-3 Sulfosuccinate (39%) | 10 | Opaque |
| Sodium Methyl Oleyl Taurate Powder | 3 | Opaque |
| Lauroamphocarboxyglcinate (and) Sodium Trideceth Sulfate (37%) | 10 | Translucent |
| Sodium Lauriminodipropionate (30%) | 10 | Clear |
| Cocoamphopropionate (37%) | 10 | Translucent |
| Cocoamphocarboxyglycinate (50%) | 10 | Opaque |
| Sucrose Cocoate (100%) | 10 | Clear |
| Cocoamphocarboxypropionate (39%) | 10 | Clear, turns color unacceptable green. |

Clear liquids on visual inspection were free of any degree of haziness, graininess or opacity. Opaque liquids would not permit the clear recognition of objects, particularly reading matter. Translucent liquids lacked clarity however would allow the recognition of objects viewed through them. Observation was made immediately after preparation and at a temperature of about 25° C.

The overall best combination of clarity and foaminess was sodium lauriminodipropionate. Sucrose cocoate did not impart good foaminess to the test system. Cocoamphocarboxypropionate was not as good a cosurfactant overall for the system, primarily because of its unacceptable color.

Various quantities of sodium lauriminodipropionate (SLDP) were employed in the composition and evaluated with respect to various properties.

EXAMPLE 2

| Ingredient | % w/w |
|---|---|
| Part 1 | |
| Monolaureth-3 Phosphate | 12.20 |
| Dilaureth-3 Phosphate | 5.80 |
| PEG-40 Stearate | 3.80 |
| Polysorbate 60 | 2.50 |
| Lauric Acid | 2.00 |
| Pareth 25-7 Carboxylic Acid | 1.00 |
| Part 2 | |
| Deionized Water | q.s. to 100.00 |
| NaOH (50% aq.) | 4.85 |
| Sodium Lauriminodipropionate (30% aq.) [SLDP] | See table 2 |
| PEG-150 Distearate | 2.00 |
| Part 3 | |
| FD&C Blue #1 (0.01% aq.) | 1.20 |
| DMDM Hydantoin | 0.30 |

-continued

| Ingredient | % w/w |
|---|---|
| Fragrance | 0.30 |
| | 100.00 |

Batches were prepared as follows. Ingredients of Part 1 were weighed together and heated to 82° C.±2° C. with slow mixing. Part 2 deionized water and NaOH (50%) were then added to Part 1 and agitation increased to moderate speed. The temperature of the batch was then increased to 82° C.±2° C. and maintained at this temperature for 30 minutes. After 30 minutes, the Sodium lauriminodipropionate (SLDP) and PEG -150 Distearate were added and dissolved. The batch was then cooled to 40° C. with slow stirring and each ingredient of Part 3 was added in order. The batch was then cooled to 25° C. and evaluated for pH, viscosity and clarity immediately after preparation.

Clarity and viscosity values are given below. All pH values fell within the range of 7.5–7.7.

TABLE 2

| % SLDP | Appearance | Viscosity (cps.) |
|---|---|---|
| 0 | Clear Liquid | 11620 |
| 5 | Clear Liquid | 4440 |
| 15 | Clear Liquid | 6100 |
| 18 | Clear Liquid | 4320 |
| 20 | Hazy Liquid | 20,000 |
| 25 | Hazy Liquid | 2420 |

The desired clarity disappeared between 18 and 20 wt %. SLDP. The formulation also showed significant viscosity variation dependent upon the quantity of SLDP present. The most desired viscosity is from about 3,000 to 7,000 cps. However a viscosity from about 2,000 to 10,000 cps can be employed with facility in a liquid formulation which is pumpable by an ordinary hand operated apparatus using a reasonably sized aperture.

Foam height testing was performed on the above compositions as follows. 15 grams of cleanser were added to 84 grams of 250 ppm hard water and 1 gram of synthetic sebum. The hard water was prepared by mixing together 40 grams of MgCl 2.6H20 with 45 grams of CaCl 2.2H20 and diluting to 250 ppm. The synthetic sebum was prepared by melting together the following ingredients.

| | % by Wgt. |
|---|---|
| Palmitic Acid | 10.0 |
| Stearic Acid | 5.0 |
| Coconut Oil | 15.0 |
| Paraffin | 10.0 |
| Spermaceti | 15.0 |
| Olive Oil | 20.0 |
| Squalene | 5.00 |
| Cholesterol | 5.00 |
| Oleic Acid | 10.0 |
| Linoleic Acid | 5.0 |
| | 100.0 |

The test mixture was then heated with moderate agitation and slow heating to 105° F. This dispersion was then carefully poured into a 600 ml. graduated cylinder containing a plastic water-filled tube. The cylinder was then mounted onto the center of a Vertical Rotator Assembly and rotated at a constant speed of 30 rpm utilizing the action of the circular mixing of the cylinder and the free falling action of the water-filled tube in the cylinder. After 8 complete revolutions, the Flash Foam Height was measured and the Drainage Time was also measured. Drainage Time is defined as the time measured from the completion of the 20 revolutions to the time at which 100 mls. of apparent liquid has drained. Drainage Time is a measure of the wetness and stability of the foam. Five samples at each level of Sodium lauriminodipropionate were tested. The results of Foam Height Testing are summarized in Table 2.

TABLE 2

| % SLDP | Flash Foam (mls.) | Max. Foam (mls.) | Drainage Time (sec.) |
|---|---|---|---|
| 0 | 196 | 228 | 14 |
| 5 | 204 | 238 | 18.4 |
| 15 | 244 | 325 | 35.4 |
| 18 | 259 | 354 | 36.6 |

Significantly different results (95% confidence) were observed for the following levels of Sodium lauriminodipropionate for the following Foam Height parameters.

| 0% vs 15% | Flash Foam, Maximum Foam & Drainage Time |
|---|---|
| 0% vs 18% | Flash Foam, Maximum Foam & Drainage Time |

The SLDP clearly brings about a significantly better foaming composition in the same wt % ranges wherein clarity is preserved.

Although not necessary to achieve the desired foaming characteristics a small amount of a traditional soap, that is an alkali metal salt of a fatty acid such as sodium or potassium laurate, myristate, palmitate, stearate and the like can also be present in the composition to achieve additional foaming behavior. Quantities of soap of from about 0.5 to 10 wt %, preferably 1–6 wt %. of the composition can be present. Relatively small quantities of soap are used so as to maintain the low irritancy, and excellent mildness of the composition.

EXAMPLE 3

Sodium Laurate at a low level was evaluated as an auxilliary surfactant as demonstrated in the following example.

| Example 3 Ingredient | 3-1 % w/w | 3-2 % w/w |
|---|---|---|
| Part 1 | | |
| Monolaureth-3 Phosphate | 13.80 | 12.60 |
| Dilaureth-3 Phosphate | 6.20 | 5.40 |
| PEG-40 Stearate | 3.00 | 3.00 |
| Polysorbate 60 | 2.50 | 2.50 |
| PEG-25 Hydrogenated Castor Oil | 2.00 | 2.00 |
| Pareth 25-7 Carboxylic Acid | 1.00 | 1.00 |
| PEG-150 Distearate | 3.00 | 3.00 |
| Lauric Acid | 0.00 | 2.00 |
| Part 2 | | |
| Deionized Water | 57.85 | 57.35 |
| NaOH (50% aq.) | 4.85 | 5.15 |
| EDTA-Disodium salt | 0.00 | 0.20 |
| Part 3 | | |
| Deionized Water | 4.00 | 4.00 |
| FD&C Blue #1 (0.01% aq.) | 1.20 | 1.20 |
| Part 4 | | |
| DMDM Hydantoin | 0.30 | 0.30 |
| Fragrance | 0.30 | 0.30 |
| | 100.00 | 100.00 |

| Example 3 Ingredient | 3-1 % w/w | 3-2 % w/w |
|---|---|---|
| pH (10% aq.) | 7.5 | 7.8 |

Both samples were clear liquids and were prepared as given in Example 1.

Foam height testing was performed on the above compositions as follows. 15 grams of cleanser were added to 84 grams of 250 ppm hard water and 1 gram of Synthetic Sebum. The hard water was prepared by mixing together 40 grams of $MgCl_2$ $2.6H_2O$ with 45 grams of $CaCl$ $2.2H_2O$ and diluting to 250 ppm. The Synthetic Sebum was prepared as in Example 2 above.

Foaming performance of the above formulas were run in triplicate and the results given in Table 3 below.

TABLE 3

| Sample | Flash Foam (mls.) | Max. Foam (mls.) | Drainage Time (sec.) |
|---|---|---|---|
| 3-1 | 172 | 173 | <8 |
| 3-2 | 223 | 275 | 28 |

The incorporation of this auxilliary surfactant improved the performance of the formula even in the presence of a slightly lower level of the Laureth-3 Phosphate blend.

EXAMPLE 4

In the course of experimentation it was surprisingly discovered that an additional factor also affected the viscosity of the composition as shown below in Example 4. Often the source of the base which brings about the desired alkaline pH of a formulation has no other effect on the composition. However, in the compositions of this invention, the source of the base can affect the viscosity of the composition.

| Ingredient | 4-1 | 4-2 | 4-3 |
|---|---|---|---|
| Part 1 | | | |
| Monolaureth-3 Phosphate | 12.60 | 11.88 | 12.42 |
| Dilaureth-3 Phosphate | 5.40 | 6.12 | 5.58 |
| PEG-40 Stearate | 3.00 | 3.00 | 3.00 |
| Polysorbate 60 | 2.50 | 2.50 | 2.50 |
| PEG-25 Hydrogenated Castor Oil | 2.00 | 2.00 | 2.00 |
| Pareth 25-7 Carboxylic Acid | 1.00 | 1.00 | 1.00 |
| PEG-150 Distearate | 3.00 | 3.00 | 3.00 |
| Lauric Acid | 2.00 | 2.00 | 2.00 |
| Part 2 | | | |
| Deionized Water | 57.35 | 55.90 | 57.40 |
| NaOH (50% aq.) | 5.15 | — | — |
| KOH (50% aq.) | — | 6.80 | — |
| TEA (99%) | — | — | 9.30 |
| EDTA.Na2 | 0.20 | — | — |
| Part 3 | | | |
| Deionized Water | 4.00 | 4.00 | 4.00 |
| FD&C Blue #1 (0.01% aq.) | 1.20 | 1.20 | 1.20 |
| Part 4 | | | |
| DMDM Hydantoin | 0.30 | 0.30 | 0.30 |
| Fragrance | 0.30 | 0.30 | 0.30 |
| | 100.00 | 100.00 | 100.00 |

All batches were prepared as described in Example 1. Results are given in Table 4.

TABLE 4

| Sample # | pH (10% aq.) | Description |
|---|---|---|
| 3-1 | 7.8 | Clear thin liquid |
| 3-2 | 7.9 | Clear viscous liquid |

TABLE 4-continued

| Sample # | pH (10% aq.) | Description |
|---|---|---|
| 3-3 | 7.0 | Clear thin liquid, but turns blue-green |

In this system the alkali metal potassium brought about a more desirable viscosity for the tested formulation than either sodium or an amine, specifically triethanolamine.

EXAMPLE 5

Utilizing a preferred formulation with cosurfactant b, the effect of different levels of the Laureth-3 Phosphate blend was evaluated as shown below.

| Ingredient | % w/w |
|---|---|
| Part 1 | |
| Monolaureth-3 Phosphate | See |
| Dilaureth-3 Phosphate | Table 5 |
| PEG-40 Stearate | 3.00 |
| Polysorbate 60 | 2.50 |
| Lauric Acid | 2.00 |
| Pareth 25-7 Carboxylic Acid | 1.00 |
| Part 2 | |
| Deionized Water | q.s. to 100.00 |
| NaOH (50% aq.) | 4.85 |
| Sodium Lauriminodipropionate (30% aq.) | 15.00 |
| PEG-150 Distearate | 2.00 |
| Part 3 | |
| FD&C Blue #1 (0.01% aq.) | 1.20 |
| DMDM Hydantoin | 0.30 |
| Fragrance | 0.30 |
| | 100.00 |

Batches were prepared as described in Example 2. All pH's fell within the range of 7.0-7.6. Clarity and viscosity values immediately after manufacture are given in Table 5 below.

TABLE 5

| Laureth-3 Phosphate | | | | |
|---|---|---|---|---|
| % Mono | % Di | Total | Appearance | Viscosity (cps.) |
| 6.1 | 2.9 | 9.0 | Hazy Liquid | 1580 |
| 6.8 | 3.2 | 10.0 | Clear Liquid | 2560 |
| 8.1 | 3.9 | 12.0 | Clear Liquid | 2620 |
| 12.2 | 5.8 | 18.0 | Clear Liquid | 6100 |
| 12.9 | 6.1 | 19.0 | Hazy Liquid | >20,000 |
| 13.22 | 6.28 | 19.5 | Hazy Liquid | >20,000 |
| 14.2 | 6.8 | 21.0 | Thick paste | >20,000 |

As demonstrated by the above data, the clarity of the composition is effected by the quantity of laureth-3-phosphate present. Generally it is preferred to maintain the quantity of laureth-3 phosphate surfactants below a level of 19 wt %. Not only is the clarity effected but the viscosity of the composition increases substantially between 18 and 19 wt. % phosphate.

EXAMPLE 6

Additional auxiliary surfactants were evaluated as described in Example 6 given below.

| Ingredient | % w/w |
|---|---|
| Part 1 | |
| Monolaureth-3 Phosphate | 12.24 |
| Dilaureth-3 Phosphate | 5.76 |
| PEG-40 Stearate | 3.00 |
| Polysorbate 60 | 2.50 |
| Lauric Acid | 2.00 |
| Pareth 25-7 Carboxylic Acid | 1.00 |
| Part 2 | |
| Dionized Water | q.s. to 100.00 |
| NaOH (50% aq.) | 4.85 |
| Sodium Lauriminodipropionate (30% aq.) | 15.00 |
| Auxiliary surfactant | See Table 6 |
| PEG-150 Distearate | 1.00 |
| Part 3 | |
| FD&C Blue #1 (0.01% aq.) | 1.20 |
| DMDM Hydantoin | 0.30 |
| Fragrance | 0.30 |
| | 100.00 |

Batches were prepared as described in Example 2. Final pH's fell within the range 7.3-7.4.

TABLE 6

| Auxiliary Surfactant | % by wgt. | Viscosity | Description | Comments |
|---|---|---|---|---|
| Disodium Cocamido MIPA (Mono Isopropanol Amine) Sulfosuccinate (40%) | 6.00 | 2300 cps. | Clear | |
| Triethanolamine Lauryl Sulfate (40%) | 6.00 | 3940 | Clear | |
| Sodium Laureth-3 Sulfate (29%) | 10.00 | 13220 | Hazy | |
| Disodium Laureth-3 Sulfosuccinate (39%) | 6.00 | 680 | Clear | |
| PEG-30 Glyceryl Monococoate | 3.00 | 3000 | Clear | Poor Foaming & freeze thaw |
| Disodium Lauryl Sulfosuccinate | 3.00 | 2600 | Clear | Difficult to Process |

As is observed from the data, few surfactants are capable of the requirements of clarity and viscosity without other attendant problems. The long chain alkyl amido succinates, preferably sulfosuccinates have this ability as well as the long chain alkyl sulfates. Generally, the chain length is from about ten to twenty carbon atoms in length and are normal or branched with normal or only slight branching preferred.

Incorporation of the preferred cosurfactant and auxiliary surfactants is demonstrated in Example 7 below.

EXAMPLE 7

| Ingredient | % w/w |
|---|---|
| Part 1 | |
| Monolaureth-3 Phosphate | 10.35 |
| Dilaureth-3 Phosphate | 4.65 |
| PEG-40 Stearate | 3.00 |
| Polysorbate 60 | 2.50 |
| Lauric Acid | 2.00 |
| Pareth 25-7 Carboxylic Acid | 1.00 |
| Part 2 | |
| Deionized Water | 37.255 |
| KOH (50% aq.) | 5.42 |
| Part 3 | |
| Sodium Lauriminodipropionate (30% aq.) | 15.00 |
| Triethanolamine Lauryl Sulfate (40% aq.) | 7.50 |
| Disodium Cocamido MIPA Sulfosuccinate (40% aq.) | 10.00 |
| Benzophenone-4 | 0.10 |
| Part 4 | |
| Urea | 0.50 |
| Part 5 | |
| FD&C Red #4 (0.1% aq.) | 0.075 |
| D&C Red #33 (0.10% aq.) | 0.050 |
| DMDM Hydantoin | 0.30 |

| Ingredient | % w/w |
|---|---|
| Fragrance | 0.30 |
| | 100.00 |

Example 7 was prepared as follows. Ingredients of Part 1 were weighed together and heated to 82° C.±2 C. with slow mixing. Part 2 ingredients were premixed and heated to 50° C.±2° C. with slow mixing. Part 2 was then added to Part 1 with moderate agitation and the combined phases maintained at 82° C.±2° C. for 30 minutes. After 30 minutes at 80°-84° C., each ingredient of Part 3 was added in order, one by one, insuring complete solution of each ingredient before adding the next. After addition of Benzophenone-4, the batch was cooled to 60° C. with moderate mixing (less than 1° C. per minute). When the batch reached 60° C., Part 4 was added and dissolved. The batch was then cooled at a moderate rate to 40° .C with slow mixing to avoid aeration. At 40° C., each ingredient of Part 5 was added in order insuring solution of each ingredient before adding the next. The batch was then cooled to 25° C. and evaluated for pH, viscosity and clarity immediately after preparation.

The cleanser was a clear viscous liquid with a viscosity of 5660 cps. and a pH (10% aq.) of 7.0

The minimum effective level of Sodium Lauriminodipropionate was evaluated in the preferred embodiment in Example 8 below.

EXAMPLE 8

| Ingredient | % w/w |
|---|---|
| Part 1 | |
| Monolaureth-3 Phosphate | 10.28 |
| Dilaureth-3 Phosphate | 4.72 |
| PEG-40 Stearate | 3.00 |
| Polysorbate 60 | 2.50 |
| Lauric Acid | 2.00 |
| Pareth 25-7 Carboxylic Acid | 1.00 |
| Part 2 | |
| Deionized Water | q.s. to 100.00 |
| KOH (50% aq.) | 5.42 |
| Part 3 | |
| Sodium Lauriminodipropionate (30% aq.) | See Table 8-1 |
| Triethanolamine Lauryl Sulfate (40% aq.) | 7.50 |
| Disodium Cocamido MIPA Sulfosuccinate (40% aq.) | 10.00 |
| Benzophenone-4 | 0.10 |
| Part 4 | |
| Urea | 0.50 |
| Part 5 | |
| FD&C Red #4 (0.1% aq.) | 0.075 |
| D&C Red #33 (0.10% aq.) | 0.500 |
| DMDM Hydantoin | 0.30 |
| Fragrance | 0.30 |
| | 100.00 |

Viscosity and clarity immediately after preparation are summarized in Table 8-A. All pH values fell within the range of 7.0–7.1.

TABLE 8-A

| % SLDP (30%) | Appearance | Viscosity (cps.) |
|---|---|---|
| 0 | Clear Liquid | 15940 |
| 5 | Clear Liquid | 6000 |
| 10 | Clear Liquid | 6360 |
| 15 | Clear Liquid | 5680 |

Foam Height Testing was conducted as described in Example 1. Five samples at each level of Sodium lauriminodipropionate were tested. The results of Foam Height Testing are summarized in Table 8-B.

TABLE 8-B

| SLDP (30%) | Flash Foam (mls.) | Max. Foam (mls.) | Drainage Time (sec.) |
|---|---|---|---|
| 0 | 366 | 476 | 32.6 |
| 5 | 374 | 520 | 33.6 |
| 10 | 370 | 524 | 35.2 |
| 15 | 471 | 572 | 34.8 |

Significantly different results (95% confidence) were observed for the following levels of Sodium lauriminodipropionate.

| | |
|---|---|
| 0% vs. 5% | Maximum Foam |
| 0% vs. 10% | Maximum Foam |
| 0% vs. 15% | Flash Foam, Maximum Foam |

The following formulations were prepared to test the effect of various components on properties such as clarity, viscosity, freeze-thaw stability. These formulations were prepared in a similar manner as Example 2.

TABLE 8-1

| Ingredient | 8-1 | 8-2 | 8-3 | 8-4 | 8-5 | 8-6 | 8-7 |
|---|---|---|---|---|---|---|---|
| Part 1 | | | | | | | |
| Monolaureth-3 Phosphate | 12.24 | 10.35 | 10.35 | 10.35 | 10.35 | 10.35 | 10.35 |
| Dilaureth-3 Phosphate | 5.76 | 4.65 | 4.65 | 4.65 | 4.65 | 4.65 | 4.65 |
| PEG-40 Stearate | 3.00 | 3.00 | 3.00 | 3.00 | 3.00 | 3.00 | 3.00 |
| Polysorbate 60 | 2.50 | 2.50 | 2.50 | 2.50 | 2.50 | 2.50 | 2.50 |
| Lauric Acid | 2.00 | 2.00 | 2.00 | 2.00 | 2.00 | 2.00 | 2.00 |
| Pareth 25-7 Carboxylic Acid | 1.00 | 1.00 | 1.00 | 1.00 | 1.00 | 1.00 | 1.00 |
| Part 2 | | | | | | | |
| Deionized Water | 44.85 | 35.86 | 35.63 | 31.63 | 31.505 | 30.63 | 30.255 |
| NaOH (50% aq.) | 4.85 | 0.00 | 0.00 | 0.00 | 0.00 | 0.00 | 0.00 |
| KOH (50% aq.) | 0.00 | 5.42 | 5.42 | 5.42 | 5.42 | 5.42 | 5.42 |
| Dipropylene Glycol | 0.00 | 4.00 | 4.00 | 4.00 | 4.00 | 5.00 | 5.00 |
| Part 3 | | | | | | | |
| Sodium Lauriminodi-propionate (30% aq.) | 15.00 | 15.00 | 15.00 | 15.00 | 15.00 | 15.00 | 15.00 |
| Triethanolamine Lauryl Sulfate (40% aq.) | 0.00 | 7.50 | 7.50 | 7.50 | 7.50 | 7.50 | 7.50 |
| Disodium Cocamido MIPA Sulfosuccinate (40% aq.) | 6.00 | 6.00 | 6.00 | 10.00 | 10.00 | 10.00 | 10.00 |
| PEG-150 Distearate | 1.00 | 2.00 | 2.00 | 2.00 | 2.25 | 2.00 | 2.50 |

TABLE 8-1-continued

| Ingredient | 8-1 | 8-2 | 8-3 | 8-4 | 8-5 | 8-6 | 8-7 |
|---|---|---|---|---|---|---|---|
| Benzophenone-4 | 0.00 | 0.00 | 0.10 | 0.10 | 0.10 | 0.10 | 0.10 |
| Part 4 | | | | | | | |
| Color Solution | 1.20 | 0.12 | 0.25 | 0.25 | 0.125 | 0.25 | 0.125 |
| DMDM Hydantoin | 0.30 | 0.30 | 0.30 | 0.30 | 0.30 | 0.30 | 0.30 |
| Fragrance | 0.30 | 0.30 | 0.30 | 0.30 | 0.30 | 0.30 | 0.30 |
| | 100.00 | 100.00 | 100.00 | 100.00 | 100.00 | 100.00 | 100.00 |

TABLE 8-2

| Sample # | Clarity | Freeze/thaw (3 cycles) | pH (10% aq.) | Viscosity of Mixed Phases | Final Viscosity cps. |
|---|---|---|---|---|---|
| 8-1 | Clear | Hazy | 7.51 | Fluid | 3160 |
| 8-2 | Clear | Clear | 7.16 | Fluid | 6000 |
| 8-3 | Clear | Clear | 7.11 | Fluid | 4800 |
| 8-4 | Clear | Clear | 7.11 | Fluid | 5200 |
| 8-5 | Hazy | — | — | Fluid | — |
| 8-6 | Clear | Clear | 7.10 | Fluid | 3520 |
| 8-7 | Hazy | — | 7.03 | Fluid | 4140 |

TABLE 8-4

| Sample # | Clarity | Freeze/thaw (3 cycles) | pH (10% aq.) | Viscosity of Final Phases | Viscosity (cps.) |
|---|---|---|---|---|---|
| 8-8 | Clear | Hazy | 7.06 | Fluid | 8460 |
| 8-9 | Clear | Clear | 7.02 | Fluid | 5460 |
| 8-10 | Clear | Clear | 7.08 | Fluid | 2460 |
| 8-11 | Clear | Clear | 7.00 | Fluid | 5200 |
| 8-12 | Hazy | — | — | Fluid | — |
| 8-13 | Hazy | — | 7.01 | Fluid | 6180 |

TABLE 8-3

| Ingredient | 8-8 | 8-9 | 8-10 | 8-11 | 8-12 | 8-13 |
|---|---|---|---|---|---|---|
| Part 1 | | | | | | |
| Monolaureth-3 Phosphate | 10.35 | 10.35 | 10.35 | 10.35 | 10.35 | 10.35 |
| Dilaureth-3 Phosphate | 4.65 | 4.65 | 4.65 | 4.65 | 4.65 | 4.65 |
| PEG-40 Stearate | 3.00 | 3.00 | 3.00 | 3.00 | 3.00 | 3.00 |
| Polysorbate 60 | 2.50 | 2.50 | 2.50 | 2.50 | 2.50 | 2.50 |
| Lauric Acid | 2.00 | 2.00 | 2.00 | 2.00 | 2.00 | 2.00 |
| Pareth 25-7 Carboxylic Acid | 1.00 | 1.00 | 1.00 | 1.00 | 1.00 | 1.00 |
| Part 2 | | | | | | |
| Deionized Water | 35.86 | 34.755 | 31.86 | 30.755 | 30.505 | 30.255 |
| KOH (50% aq.) | 5.42 | 5.42 | 5.42 | 5.42 | 5.42 | 5.42 |
| Butylene Glycol | 4.00 | 5.00 | 5.00 | 5.00 | 5.00 | 5.00 |
| Part 3 | | | | | | |
| Sodium Lauriminodi-propionate (30% aq.) | 15.00 | 15.00 | 15.00 | 15.00 | 15.00 | 15.00 |
| Triethanolamine Lauryl Sulfate (40% aq.) | 7.50 | 7.50 | 7.50 | 7.50 | 7.50 | 7.50 |
| Disodium Cocamido MIPA Sulfosuccinate (40% aq.) | 6.00 | 6.00 | 10.00 | 10.00 | 10.00 | 10.00 |
| PEG-150 Distearate | 2.00 | 2.00 | 1.00 | 2.00 | 2.25 | 2.50 |
| Benzophenone-4 | 0.00 | 0.10 | 0.00 | 0.10 | 0.10 | 0.10 |
| Part 4 | | | | | | |
| Color Solution | 0.12 | 0.125 | 0.12 | 0.125 | 0.125 | 0.125 |
| DMDM Hydantoin | 0.30 | 0.30 | 0.30 | 0.30 | 0.30 | 0.30 |
| Fragrance | 0.30 | 0.30 | 0.30 | 0.30 | 0.30 | 0.30 |
| | 100.00 | 100.00 | 100.00 | 100.00 | 100.00 | 100.00 |

TABLE 8-5

| Ingreient | 8-14 | 8-15 | 8-16 | 8-17 | 8-18 | 8-19 |
|---|---|---|---|---|---|---|
| Part 1 | | | | | | |
| Monolaureth-3 Phosphate | 10.35 | 10.35 | 10.35 | 10.35 | 10.35 | 10.35 |
| Dilaureth-3 Phosphate | 4.65 | 4.65 | 4.65 | 4.65 | 4.65 | 4.65 |
| PEG-40 Stearate | 3.00 | 3.00 | 3.00 | 3.00 | 3.00 | 3.00 |
| Polysorbate 60 | 2.50 | 2.50 | 2.50 | 2.50 | 2.50 | 2.50 |
| Lauric Acid | 2.00 | 2.00 | 2.00 | 2.00 | 2.00 | 2.00 |
| Pareth 25-7 Carboxylic Acid | 1.00 | 1.00 | 1.00 | 1.00 | 1.00 | 1.00 |
| Part 2 | | | | | | |
| Deionized Water | 39.36 | 35.255 | 36.255 | 37.255 | 34.005 | 34.255 |
| KOH (50% aq.) | 5.42 | 5.42 | 5.42 | 5.42 | 5.42 | 5.42 |
| Butylene Glycol | 0.00 | 0.00 | 0.00 | 0.00 | 0.00 | 2.00 |
| Part 3 | | | | | | |
| Sodium Lauriminodi-propionate (30% aq.) | 15.00 | 15.00 | 15.00 | 15.00 | 15.00 | 15.00 |
| Triethanolamine Lauryl Sulfate (40% aq.) | 7.50 | 7.50 | 7.50 | 7.50 | 7.50 | 7.50 |
| Disodium Cocamido MIPA Sulfosuccinate (40% aq.) | 6.00 | 10.00 | 10.00 | 10.00 | 10.00 | 10.00 |
| PEG-150 Distearate | 2.00 | 2.00 | 1.00 | 0.00 | 0.25 | 1.00 |
| Benzophenone-4 | 0.00 | 0.10 | 0.10 | 0.10 | 0.10 | 0.10 |
| Part 4 | | | | | | |

TABLE 8-5-continued

| Ingreient | 8-14 | 8-15 | 8-16 | 8-17 | 8-18 | 8-19 |
|---|---|---|---|---|---|---|
| Urea | 0.50 | 0.50 | 0.50 | 0.50 | 0.50 | 0.50 |
| Part 4 | | | | | | |
| Color Solution | 0.12 | 0.125 | 0.125 | 0.125 | 0.125 | 0.125 |
| DMDM Hydantoin | 0.30 | 0.30 | 0.30 | 0.30 | 0.30 | 0.30 |
| Fragrance | 0.30 | 0.30 | 0.30 | 0.30 | 0.30 | 0.30 |
| | 100.00 | 100.00 | 100.00 | 100.00 | 100.00 | 100.00 |

TABLE 8-6

| Sample # | Clarity | Freeze/thaw (3 cycles) | pH (10% aq.) | Viscosity of Final Phases | Viscosity (cps.) |
|---|---|---|---|---|---|
| 8-14 | Clear | Clear | 7.12 | Fluid | 17380 |
| 8-15 | Hazy | — | 6.95 | Moderately Viscous | >20000 |
| 8-16 | Clear | Clear | 7.07 | Moderately Viscous | 14820 |
| 8-17 | Clear | Clear | 7.00 | Fluid | 5660 |
| 8-18 | Clear | Clear | 7.01 | Fluid | 7960 |
| 8-19 | Clear | Clear | 7.19 | Fluid | 8560 |

As can be seen, the level of viscosity builder PEG-150 Distearate can affect clarity as well as viscosity. Butylene glycol, Dipropylene glycol and Urea all improve freeze/thaw stability testing and Butylene glycol and Dipropylene Glycol improve clarity and processability. These glycols also can adversely affect viscosity. The level of water in the system affects the clarity of the system and the processability on mixing of Part 2 to Part 1.

With respect to the viscosity builder, a polyoxyethylglycol di long chain ester is preferred. The number of ethoxy groups are from about 75 to 225, preferably 125 to 200. The long chain ester grouping is generally an alkyl having from about ten to about twenty carbon atoms, preferably normal alkyl.

EXAMPLE 9

Below is an example of a mild baby shampoo exemplification of the formulation.

| Ingredient | % w/w |
|---|---|
| Part 1 | |
| Monolaureth-3 Phosphate | 12.24 |
| Dilaureth-3 Phosphate | 5.76 |
| PEG-40 Stearate | 3.00 |
| Polysorbate 60 | 2.50 |
| Lauric Acid | 2.00 |
| Pareth 25-7 Carboxylic Acid | 1.00 |
| Part 2 | |
| Deionized Water | 47.85 |
| NaOH (50% aq.) | 4.85 |
| Sodium Lauriminodipropionate (30% aq.) | 15.00 |
| PEG-30 Glyceryl Monococoate | 3.00 |
| PEG-150 Distearate | 1.00 |
| Part 3 | |
| FD&C Blue #1 (0.01% aq.) | 1.20 |
| DMDM Hydantoin | 0.30 |
| Fragrance | 0.30 |
| | 100.00 |

A clear, moderately viscous liquids is obtained. An appropriate viscosity and pH is obtained. It provides adequate foaming for gentle cleaning of the hair.

EXAMPLE 10

Below is an example of a mild bubble bath.

| Ingredient | % w/w |
|---|---|
| Part 1 | |
| Monolaureth-3 Phosphate | 12.24 |
| Dilaureth-3 Phosphate | 5.76 |
| PEG-40 Stearate | 3.00 |
| Polysorbate 60 | 2.50 |
| Lauric Acid | 2.00 |
| Pareth 25-7 Carboxylic Acid | 1.00 |
| Part 2 | |
| Deionized Water | 37.85 |
| NaOH (50% aq.) | 4.85 |
| Sodium Lauriminodipropionate (30% aq.) | 15.00 |
| Disodium Cocamido MIPA Sulfocsuccinate (40% aq.) | 3.00 |
| Disodium Lauryl Sulfosuccinate Powder | 2.25 |
| PEG-150 Distearate | 1.00 |
| Part 3 | |
| FD&C Blue #1 (0.01% aq.) | 1.20 |
| DMDM Hydantoin | 0.30 |
| Fragrance | 0.30 |
| | 100.00 |

A clear, moderately viscous liquid is obtained. An appropriate viscosity and pH is present. It provides creamy foaming for bathing.

EXAMPLE 11

A creamy body cleanser is prepared.

| Ingredient | % w/w |
|---|---|
| Part 1 | |
| Monolaureth-3 Phosphate | 12.42 |
| Dilaureth-3 Phosphate | 5.58 |
| PEG-40 Stearate | 3.00 |
| Polysorbate 60 | 2.50 |
| Lauric Acid | 2.00 |
| Pareth 25-7 Carboxylic Acid | 1.00 |
| Part 2 | |
| Deionized Water | 30.85 |
| NaOH (50% aq.) | 4.85 |
| Sodium Lauriminodipropionate (30% aq.) | 15.00 |
| Triethanolamine Lauryl Sulfate (40%) | 20.00 |
| PEG-150 Distearate | 1.00 |
| Part 3 | |
| FD&C Blue #1 (0.01% aq.) | 1.20 |
| DMDM Hydantoin | 0.30 |
| Fragrance | 0.30 |
| | 100.00 |

EXAMPLE 12

A creamy body cleanser is prepared.

| Ingredient | % w/w |
|---|---|
| Part 1 | |
| Monolaureth-3 Phosphate | 12.24 |
| Dilaureth-3 Phosphate | 5.76 |
| PEG-40 Stearate | 3.00 |
| Polysorbate 60 | 2.50 |

-continued

| Ingredient | % w/w |
|---|---|
| Lauric Acid | 2.00 |
| Pareth 25-7 Carboxylic Acid | 1.00 |
| Part 2 | |
| Deionized Water | 37.75 |
| NaOH (50% aq.) | 4.95 |
| Triethanolamine Lauryl Sulfate (40%) | 3.00 |
| Sodium Lauriminodipropionate (30% aq.) | 15.00 |
| Disodium Lauryl Sulfosuccinate | 2.25 |
| PEG-150 Distearate | 1.00 |
| Part 3 | |
| FD&C Blue #1 (0.01% aq.) | 1.20 |
| DMDM Hydantoin | 0.30 |
| Fragrance | 0.30 |
| | 100.00 |

A creamy, viscous paste is prepared. Appropriate viscosity and pH is obtained. It provides creamy foam for gentle cleaning of the body.

It should be noted that 0.75 wt. % of butylene glycol can be added to Example 7 and 8 at Part 2 to improve the processing.

I claim:

1. A composition suitable for topical application to the skin or hair comprising an admixture of
   a. phosphate surfactant mixture of the structure

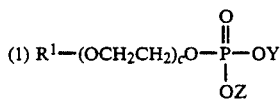

and

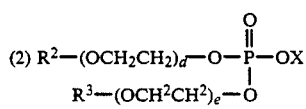

wherein $R^1$ is normal alkyl having an average of from about 10 to 18 carbon atoms;

$R^2$ and $R^3$ are the same or different and are normal alkyl having an average of about 10 to 18 carbon atoms;

X, Y and Z are the same or different and are selected from hydrogen, alkali metal, alkaline earth metal, ammonium and substituted ammonium cations;

d and e are the same or different and are selected from 0 or an integer from 1 to 10 ; and c is 0 or an integer from 1 to 4; wherein with respect to a (1) and a (2) taken together the wt % of a (1) is from about 55 to 75 wt % and a (2)is from about 25 to 45 wt %, and b. a cosurfactant of the formula

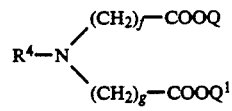

wherein $R^4$ is normal alkyl having an average of from about 10 to 18 carbon atoms;

f and g are the same or different and are 1 or 2;

Q and $Q^1$ are the same or different and are selected from hydrogen, alkali metal, ammonium, and substituted ammonium cation with the proviso that Q and $Q^1$ are not hydrogen at the same time; wherein with respect to a and b taken together, a is from about 33 to 95 wt % and b is from about 5 to 67 wt %.

2. The composition in accordance with claim 1 wherein the composition is visually clear.

3. The composition in accordance with claim 2 wherein the composition has a viscosity of from about 2,000 to about 10,000 cps.

4. The composition in accordance with claim 1 wherein a soap is also present.

5. The composition in accordance with claim 4 wherein the soap is present in about 1 to 10wt % of the composition.

6. The composition in accordance with claim 4 wherein the soap is present in about 2 to about 6 wt. % of the composition.

7. The composition in accordance with claim 2 wherein a thickening agent is also present.

8. The composition in accordance with claim 7 wherein the thickening agent is a polyoxyethylene di long chain ester.

9. The composition in accordance with claim 8 wherein the thickening agent is less than about 3 wt % of the composition.

10. The composition in accordance with claim 5 wherein at least one additional surfactant is present.

11. The composition in accordance with claim 10 wherein a long chain alkyl sulfate salt is present.

12. The composition in accordance with claim 10 wherein a long chain amido sulfosuccinate salt is also present.

13. The composition in accordance with claim 11 wherein a long chain amido amine sulfosuccinate salt is also present.

14. The composition in accordance with claim 1 wherein the composition is not clear.

15. The composition in accordance with claim 1 as a facial or hand cleanser.

16. The composition in accordance with claim 2 as a facial or hand cleanser.

* * * * *